United States Patent [19]

Fortin et al.

[11] Patent Number: 5,674,883
[45] Date of Patent: Oct. 7, 1997

[54] DERIVATIVES OF PYRIDONE, THEIR PREPARATION PROCESS, THE NEW INTERMEDIATES OBTAINED, THEIR USE AS MEDICAMENTS AND THE PHARMACEUTICAL COMPOSITIONS CONTAINING THEM

[75] Inventors: Michel Fortin, Paris; Jean Luc Haesslein, Courtry; Bertrand Heckmann, Cachan, all of France

[73] Assignee: Roussel Uclaf, France

[21] Appl. No.: 690,552

[22] Filed: Jul. 31, 1996

Related U.S. Application Data

[63] Continuation of Ser. No. 446,471, May 22, 1995, abandoned, which is a continuation of Ser. No. 122,498, filed as PCT/FR93/00118, Feb. 5, 1993, published as WO93/16049, Aug. 19, 1993, abandoned.

[30] Foreign Application Priority Data

Feb. 7, 1992 [FR] France ................... 92 01390

[51] Int. Cl.[6] ............ A61K 31/44; C07D 401/10
[52] U.S. Cl. .......... 514/340; 514/235.5; 514/235.8; 514/236.2; 514/318; 514/343; 544/124; 546/194; 546/276; 546/281; 546/345; 546/351
[58] Field of Search .................. 546/296, 298, 546/194, 276, 281, 345, 351; 549/416, 417, 418; 514/348, 350, 235.5, 235.8, 236.2, 318, 340, 343; 544/124

[56] References Cited

U.S. PATENT DOCUMENTS

| | | | |
|---|---|---|---|
| 3,494,959 | 2/1970 | Schleppnik et al. | 549/418 |
| 5,356,911 | 10/1994 | Muller-Gliemann et al. | 514/340 |

FOREIGN PATENT DOCUMENTS

| | | |
|---|---|---|
| 0324377 | 7/1989 | European Pat. Off. . |
| 0354495 | 2/1990 | European Pat. Off. . |
| 0443568 | 8/1991 | European Pat. Off. . |
| 0445811 | 9/1991 | European Pat. Off. . |
| 0609053 | 2/1979 | Germany . |
| 0068574 | 9/1973 | Japan . |
| 9119697 | 12/1991 | WIPO . |

*Primary Examiner*—Shailendra Kumar
*Attorney, Agent, or Firm*—Bierman, Muserlian and Lucas LLP

[57] ABSTRACT

Products of formula (I):

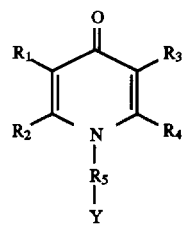

in which:

$R_1$, $R_2$, $R_3$ and $R_4$ represent:
— a hydrogen atom, a halogen atom, one of the following radicals: hydroxyl, mercapto, cyano, nitro, sulpho, formyl, benzoyl, acyl, carboxy, cycloalkyl, acyloxy,
— an alkyl, alkenyl, alkynyl, alkyloxy or alkythio radical,
— an alkyl, alkenyl, alkynyl, alkyloxy or alkylthio radical,
— an aryl, arylalkyl, arylalkenyl, aryloxy or arylthio radical,
— a radical:

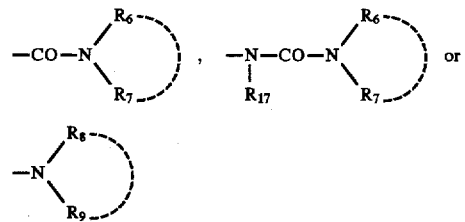

—a—$(CH_2)_{m1}$—$S(O)_{m2}$—Z'—$R'_{14}$ radical in which m1 represents an integer from 0 to 4, m2 represents an integer from 0 to 2, $R_5$ represents a divalent alkylene radical, Y represents the —$Y_1$—B—$Y_2$ radical.

These products have useful pharmacological properties, which justify their use as medicaments.

15 Claims, No Drawings

DERIVATIVES OF PYRIDONE, THEIR PREPARATION PROCESS, THE NEW INTERMEDIATES OBTAINED, THEIR USE AS MEDICAMENTS AND THE PHARMACEUTICAL COMPOSITIONS CONTAINING THEM

PRIOR APPLICATIONS

This application is a continuation of U.S. patent application Ser. No. 446,471 filed May 22, 1995, now abandoned, which is a continuation of U.S. patent application Ser. No. 122,498 filed Sep. 27, 1993, now abandoned, which is a 371 of PCT/FR93/00118, filed Feb. 5, 1993, published as WO93/16049 Aug. 19, 1993.

The present invention relates to new derivatives of pyridone, their preparation process, the new intermediates obtained, their use as medicaments and the pharmaceutical compositions containing them.

A subject of the present invention is the products of formula (I):

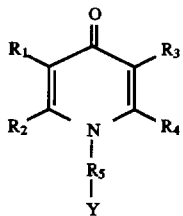

in which:

$R_1$, $R_2$, $R_3$ and $R_4$, identical or different, represent:

a) a hydrogen atom, a halogen atom, one of the following radicals: hydroxyl, mercapto, cyano, nitro, sulpho, formyl, benzoyl, acyl having at most 12 carbon atoms, free, salified, esterified or amidified carboxy, cycloalkyl containing 3 to 7 carbon atoms, acyloxy having at most 42 atoms b) an alkyl, alkenyl, alkynyl, alkyloxy or alkylthio radical, these radicals being linear or branched, containing at most 6 carbon atoms and being optionally substituted, c) an aryl, arylalkyl, arylalkenyl, aryloxy or arylthio radical in which the linear or branched alkyl and alkenyl radicals contain at most 6 carbon atoms, these aryl, arylalkyl, arylalkenyl or arylthio radicals being such that the aryl radical represents a monocyclic radical containing 5 or 6 links or a radical constituted by condensed rings containing 8 to 40 links, these radicals optionally containing one or more heteroatoms chosen from oxygen, nitrogen and sulphur atoms, and being optionally substituted, d) a radical

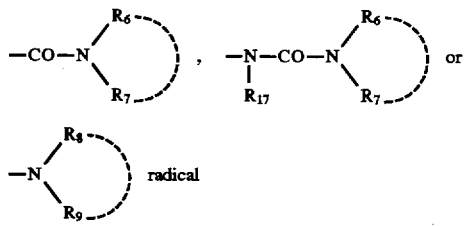

in which:

either $R_{17}$, $R_6$ and $R_7$ or $R_8$ and $R_9$, identical or different,, represent:

—a hydrogen atom,

—a free, salified, esterified or amidified carboxy radical,

—an alkyl or alkenyl radical containing at most 6 carbon atoms and optionally substituted by one or more radicals chosen from halogen atoms and the hydroxyl radical, —an alkyl or alkenyl radical containing 2 to 6 carbon atoms substituted by an alkyloxy radical containing at most 6 carbon atoms, —an aryl or arylalkyl radical in which the linear or branched alkyl radical contains at most 6 carbon atoms, the, se aryl and arylalkyl radicals being such that the aryl radical represents a monocyclic radical containing 5 or 6 links or a radical constituted by condensed rings containing 8 to 10 links, these radicals optionally containing one or more heteroatoms chosen from oxygen, nitrogen and sulphur atoms, and being optionally substituted by one or more radicals chosen from halogen atoms, the following radicals: hydroxyl, cyano, trifluoromethyl, nitro, alkyl, alkenyl, alkyloxy, alkylthio and acyl radicals, these radicals containing at most 6 carbon atoms, the free, salified or esterified carboxy radical, —a—$(CH_2)_{m1}$—$S(O)_{m2}$—Z—$R_{14}$ radical in which m1 represents an integer from 0 to 4 and m2 represents an integer from 0 to 2, preferably 2, and either —Z—$R_{14}$ represents —$NH_2$ or Z represents the —$N(R_{15})$—, —$N(R_{15})$'CO—, —$(R_{15})$—CO—$N(R_{16})$—radicals or a single bond, $R_{14}$ represents an alkyl, alkoxy, alkenyl or aryl radical, these radicals being optionally substituted and $R_{15}$ and $R_{16}$, identical or different, represent a hydrogen atom or $R_{14}$ as defined above, or $R_6$ and $R_7$ or $R_8$ and $R_9$ form respectively together with the nitrogen atom to which they are linked a monocyclic radical containing 5 or 6 links or a radical constituted by condensed rings containing 8 to 10 links, these radicals optionally containing one or more heteroatoms chosen from oxygen, nitrogen and sulphur atoms, and being optionally substituted by one or more radicals chosen from halogen atoms, the following radicals: hydroxyl, cyano, trifluoromethyl, nitro, alkyl, alkenyl, alkyloxy, alkylthio and acyl radicals, these radicals containing at most 6 carbon atoms, the free, salified or esterified carboxy radical, or $R_8$ and $R_9$, identical or different, or one of $R_6$ or $R_7$, represents an acyl radical derived from carboxylic acid containing at most 6 carbon atoms, e) a —$(CH_2)_{m1}$—$S(O)_{m2}$—Z'—$R'_{14}$ radical in which m1 represents an integer from 0 to 4, m2 represents an integer from 0 to 2 and preferably 2 such that: either when m1 is different from 0, Z'—$R'_{14}$ represents an amino radical optionally substituted by one or two radicals chosen from alkyl and alkenyl radicals and containing at most 6 carbon atoms and the phenyl radical, these radicals being themselves optionally substituted by one or more radicals chosen from halogen atoms, the hydroxyl radical, alkyl and alkoxy radicals containing at most 4 carbon atoms, the trifluoromethyl, free, salified or esterified carboxy, cyano or tetrazolyl radical or whatever the value of m1:

—$R'_{14}$ represents an alkyl or alkenyl radical containing at most 6 carbon atoms or an aryl radical, these radicals being themselves optionally substituted by one or more radicals chosen from halogen atoms, the hydroxyl radical, alkyl and alkoxy radicals containing at most 4 carbon atoms, the trifluoromethyl, free, salified, esterified or amidified carboxy, cyano or tetrazolyl radical, and Z' represents a single bond or the —$N(R'_{15})$—, $N(R'_{15})$—CO—, —$N(R'_{15})$—CO2—, —$N(R'_{15})$—CO—$N(R'_{16})$— and —$N(R'_{15})$—SO$(O)_{m3}$— radicals or —Z—$R'_{14}$ represents

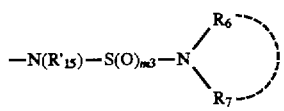

in which R'$_{15}$ and R'$_{16}$, identical or different, represent the hydrogen atom or are chosen from the values of R'$_{14}$, m3 represents an integer from 0 to 2 and R$_6$ and R$_7$ have the meanings indicated above, R$_5$ represents a linear or branched divalent alkylene radical containing at most 4 carbon atoms, Y represents the —Y$_1$—B—Y$_2$ radical in which: Y$_1$ represents a monocyclic aryl radical containing 5 or 6 links or constituted by condensed rings containing 8 to 10 links, these radicals optionally containing one or more heteroatoms chosen from oxygen, nitrogen or sulphur atoms, and being optionally substituted by one or more radicals chosen from the radicals that can be represented by R$_1$, R$_2$, R$_3$ or R$_4$, B represents: either a single bond between Y$_1$ and Y$_2$, or one of the following divalent radicals: —CO—, —NH—CO—, —CO—NH—, —O—(CH$_2$)$_n$— or —S—(CH$_2$)$_n$— with n representing the values 0 to 4, Y$_2$ represents: either, if B represents a single bond, a hydrogen or halogen atom, one of the following radicals: hydroxyl, cyano, nitre, trifluoromethyl, free, salified, esterified or amidified carboxy, tetrazole or isoxazole, or, whatever the value of B and Y$_2$ being identical to or different from Y$_1$, the values defined for Y$_1$, it being understood that R$_1$ and R$_3$ do not represent a hydrogen atom, the said products of formula (I) being in all the possible racemic, enantiomeric and diastereoisomeric isomer forms, as well as the addition salts with mineral and organic acids or with mineral and organic bases of the said products of formula (I).

Thus a subject of the present invention is the products of formula (I) as defined above, characterized in that the substituent or substituents, identical or different, that can be carried by:

a) the alkyl, alkenyl, alkynyl, alkyloxy and alkylthio radicals that can be represented by R$_3$ and R$_4$, b) the aryl, arylalkyl, arylalkenyl, aryloxy and arylthio radicals that can be represented by R$_1$, R$_2$, R$_3$ and R$_4$, c) the alkyl, alkenyl and aryl radicals that can be represented by R$_{14}$, are chosen from the group formed by:

—the halogen atoms, the following radicals: hydroxyl, cyano, nitro, formyl, acyl or acyloxy having at most 6 carbon atoms, benzoyl, carboxy free, salified or esterified by an alkyl radical containing at most 6 carbon atoms, —the alkyl and alkenyl radicals containing at most 6 carbon atoms and optionally substituted by one or more substituents chosen from the halogen atoms, the hydroxyl radical, alkyloxy radicals containing ah most 6 carbon atoms, carbamoyl, free, esterified or amidified carboxy, tetrazole, —the aryl, arylalkyl, aryloxy, arylalkoxy, arylthio and arylalkylthio radicals in which the sulphur atom can be oxidized in the form of the sulphoxide or sulphone, in which radicals the linear or branched alkyl, alkoxy and alkylthio radicals contain at most 6 carbon atoms, in all these radicals, the aryl radical represents a monocyclic radical containing 5 or 6 links or a radical constituted by condensed rings containing 8 to 10 links, all these radicals optionally containing one or more heteroatoms chosen from oxygen, nitrogen and sulphur atoms, and being optionally substituted by one or more radicals chosen from halogen atoms, the following radicals: hydroxyl, cyano, trifluoromethyl, nitro, alkyl, alkenyl, alkyloxy and acyl radical, these radicals containing at most 6 carbon atoms, free, salified, esterified or amidified carboxy radicals,

in which: either R$_{10}$ and R$_{11}$ or R$_{12}$ and R$_{13}$, identical or different, represent:

—a hydrogen atom,

—an alkyl or alkenyl radical containing at most 6 carbon atoms and optionally substituted by one or more radicals chosen from halogen atoms and the hydroxyl radical, —an alkyl or alkenyl radical containing 2 to 6 carbon atoms substituted by an alkyloxy radical containing at most 6 carbon atoms, —an aryl or arylalkyl radical in which the linear or branched alkyl radical contains at most 6 carbon atoms, these aryl and arylalkyl radicals being such that the aryl radical represents a monocyclic radical containing 5 or 6 links or a radical constituted by condensed rings containing 8 to 10 links, these radicals optionally containing one or more heteroatoms chosen from oxygen, nitrogen and sulphur atoms, and being optionally substituted by one or more radicals chosen from halogen atoms, the following radicals: hydroxyl, cyano, trifluoromethyl, nitro, alkyl, alkenyl, alkyloxy and acyl radicals, these radicals containing at most 6 carbon atoms, free, salified, esterified or amidified carboxy radicals, or R$_{10}$ and R$_{11}$ or R$_{12}$ and R$_{13}$ form respectively with the nitrogen atom to which they are linked a monocyclic radical containing 5 or 6 links or a radical constituted by condensed rings containing 8 to 10 links, these radicals optionally containing one or more heteroatoms chosen from oxygen, nitrogen and sulphur atoms, and being optionally substituted by one or more radicals chosen from halogen atoms, hydroxyl, cyano, trifluoromethyl, nitro radicals, alkyl, alkenyl, alkyloxy and acyl radicals, these radicals containing at most 6 carbon atoms, free, salified, esterified or amidified carboxy radicals, or R$_{12}$ and R$_{13}$, identical or different, or one of R$_{10}$ and R$_{11}$, represents an acyl radical derived from a carboxylic acid containing at most 6 carbon atoms, —linear and branched alkyloxy and alkylthio radicals containing at most 6 carbon atoms and optionally substituted by the radical:

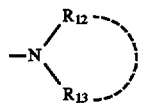

in which R$_{12}$ and R$_{13}$ have the meaning indicated above, the said products of formula (I) being in all the possible racemic, enantiomeric and diastereoisomeric isomer forms, as well as the addition salts with mineral and organic acids or with mineral and organic bases of the said products of formula (I).

A particular subject of the present invention is the products of formula (I) as defined above and corresponding to the formula (IC):

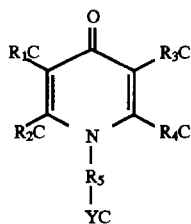

(IC)

in which:

R₁C, R₂C, R₃C and R₄C, identical or different, are chosen from the group formed by:
— the hydrogen atom,
— halogen atoms,
— the hydroxyl radical,
— the following radicals: mercapto, cyano, nitro, formyl, benzoyl, acyl having at most 6 carbon atoms, sulpho,
— carboxy radicals free, salified or esterified by a linear or branched alkyl radical containing at most 4 carbon atoms, tetrazole radicals,
— linear or branched alkyl, cycloalkyl, alkenyl, alkyloxy and alkylthio radicals containing at most 6 carbon atoms, phenyl, naphthyl, benzyl and phenylthio radicals, all these radicals being optionally substituted by one or more identical or different radicals chosen from halogen atoms, the hydroxyl radical, alkyloxy and alkylthio radicals containing at most 4 carbon atoms, these radicals being optionally substituted by an amino, mono- or dialkylamino radical in which the alkyl radical contains 1 to 4 carbon atoms, trifluoromethyl, cyano, free, salified or esterified carboxy, benzyloxy, phenoxy; benzylthio, phenylthio and pyridylthio in which the sulphur atom can be oxidized in the form of the sulphoxide or sulphone, tetrazole, isoxazole, pyrrolidinyl, pyrrolidinylcarbonyl and phenyl optionally substituted by one or more radicals chosen from halogen atoms, the hydroxyl radical, alkyl and alkoxy radicals containing at most 4 carbon atoms, —amino, mono- or dialkylamino radicals in which the alkyl radical contains 1 to 4 carbon atoms, carbamoyl, pyrrolyl, pyrrolidinyl, morpholino, piperazinyl, pyrrolylmethyl, morpholinomethyl, piperazinylmethyl, pyrrolylcarbonyl, morpholinocarbonyl, pyrrolidinylcarbonyl, piperazinylcarbonyl, all the piperazinyl radicals being optionally substituted on the second nitrogen atom by an alkyl or phenyl radical, these alkyl and phenyl radicals being themselves optionally substituted by one or more radicals chosen from hydroxyl atoms, halogen, nitro, alkyl or alkyloxy containing at most 4 carbon atoms, trifluoromethyl, cyano, free, salified or esterified carboxy, tetrazolyl and isoxazolyl, R₅ represents a linear or branched divalent alkylene radical, containing at most 4 carbon atoms, YC represents a phenyl or biphenyl radical optionally substituted by one or more radicals chosen from the following radicals: hydroxyl; halogen; alkyl, alkenyl and alkyloxy containing at most 4 carbon atoms and optionally substituted by a free, esterified or salified carboxy radical; trifluoromethyl; cyano; nitro; free, salified or esterified carboxy; tetrazole optionally protected by a triphenylmethyl radical; isoxazole;
— the —(CH₂)ₚ—SO₂—ZC—R₁₄C radical in which P represents the values 0 and 1, ZXC represents the —NH—, —NH—CO—, —NH—CO₂—, —NH—CO—NH— radical or a single bond and R₁₄C represents one of the following radicals: methyl, ethyl, propyl, vinyl, allyl, pyridyl, phenyl, benzyl, pyridylmethyl, pyridylethyl, nitropyridyl, pyrimidyl, tetrazolyl, diazolyl, piperidinyl, alkyl piperidinyl, thiazolyl, alkylthiazolyl, tetrahydrofuranyl, methyltetrahydrofuranyl; amino or carbamoyl optionally substituted by one or two radicals chosen from the —(CH₂)ₚ—SO₂—ZC—R₁₄C radicals as defined above and alkyl and alkenyl radicals containing at most 4 carbon atoms and optionally substituted;

all these radicals being optionally substituted by one or more radicals chosen from halogen atoms, the hydroxyl radical, alkyl and alkenyl, alkoxy radicals containing at most 4 carbon atoms, trifluoromethyl, cyano, free, salified or esterified carboxy or tetrazolyl radicals;

the said products of formula (IC) being in all the possible racemic, enantiomeric and diastereoisomeric isomer forms, as well as the addition salts with mineral and organic acids or with mineral and organic bases of the said products of formula (IC).

In the products of formulae (I) and (IC) and in what follows:
— the term linear or branched alkyl radical preferably designates methyl, ethyl, n-propyl, isopropyl, n-butyl, isobutyl, sec-butyl and tert-butyl radicals but can also represent a pentyl or hexyl radical and in particular isopentyl and isohexyl,
— the term linear or branched alkenyl radical preferably designates a vinyl, allyl, 1-propenyl, butenyl radical and particularly buten-1-yl, or pentenyl
— the term linear or branched alkynyl radical preferably designates an ethynyl, propargyl, butynyl or pentynyl radical,
— the term acyl radical can designate the decanoyl, dodecanoyl radical and preferably the acetyl, propionyl, butyryl or benzoyl radical, but can also represent the valeryl, hexanoyl, acryloyl, crotonoyl or carbamoyl radical: the formyl radical can also be mentioned;
— the term esterified carboxy preferably designates a lower alkyloxy carbonyl group optionally substituted as indicated above and hereafter, such as methoxycarbonyl, ethoxycarbonyl, aminoalkoxycarbonyl such as aminobutoxycarbonyl in which the amino group can be substituted or cyclized in order to take the values indicated for

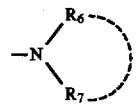

as defined above and hereafter, tert-butoxycarbonyl or a benzyloxycarbonyl group;
— the term amidified carboxy preferably designates a radical of the type

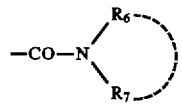

in which R₆ and R₇ have the meanings indicated above
— the term halogen atom preferably designates the chlorine atom, but can also represent a fluorine, bromine or iodine atom;
— the term cycloalkyl preferably designates a cyclopropyl, cyclopentyl or cyclohexyl radical but also cyclobutyl,
— the term acyloxy designates radicals in which the acyl radicals have the meaning indicated above and for example the acetoxy or propionyloxy radicals;
— the term linear or branched alkyloxy radical preferably designates methoxy or ethoxy radicals, but can also represent a propoxy, isopropoxy, a linear, secondary or tertiary butoxy radical, —the term linear or branched alkylthio radical designates radicals in which the alkyl radical can represent, for example, the values indicated above for the alkyl radical; the alkylthio radical preferably represents methylthio or ethylthio radicals, but can also represent a propylthio, isopropylthio, n-butylthio, sec-butylthio, tert-butylthio, isopentylthio or isohexylthio radical, —the term aryl radical designates monocyclic radicals or radicals constituted by condensed rings, carbocyclic or heterocyclic, it being understood that the heterocyclic radicals can contain one or more heteroatoms chosen from oxygen, nitrogen or sulphur atoms and that when these heterocyclic radicals contain more than one heteroatom, the heteroatoms of these heterocyclic radicals can be identical or different, —the term monocyclic radical preferably designates radicals which contain 5 or 6 links, such as a carbocyclic monocyclic radical, the phenyl radical can be mentioned; among the heterocyclic monocyclic radicals, there can be mentioned, for example, the following radicals: thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl such as delta 2-pyrrolinyl, imidazolinyl such as delta 2-imidazolinyl, pyrazolinyl such as delta 3-pyrazolinyl, as well as the isomers of position of the heteroatom or heteroatoms that can be contained by these radicals such as, for example, the tetrazolyl, isothiazolyl or isoxazolyl radicals;

—the term radical constituted by condensed rings preferably designates radicals which contain 8 to 14 links: among the radicals constituted by carbocyclic condensed rings, there can be mentioned, for example, the naphthyl and phenanthryl radicals, among the radicals constituted by heterocyclic condensed rings, there can be mentioned, for example, benzothienyl, naphtho[2,3-b]thienyl, indanyl, indenyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, pththalazinyl, naphthyridinyl, quinoxalinyl, quinazolinyl, cinnolinyl, pteridinyl, carbazolyl, beta-carbolinyl, acridnyl, phenazinyl, phenothiazinyl, phenoxazinyl, indolinyl, isoindolinyl, imidazopyridyl, imidazopyrimidinyl or also condensed polycyclic systems constituted by heterocyclic monocyclics as defined above, for example, such as for example furo[2,3-b]pyrrole or thieno[2,3-b]furan, as examples of such an aryl radical, the following radicals: can be mentioned: phenyl, naphthyl, thienyl such as thien-2-yl and thien-3-yl, furyl such as fur-2-yl, pyridyl such as pyrid-3-yl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; condensed heterocyclic groups containing at least one heteroatom chosen from sulphur, nitrogen and oxygen, for example benzothienyl such as benzothien-3-yl, benzofuryl, benzopyrrolyl, benzimidazolyl, benzoxazolyl, thionaphthyl, indolyl or purinyl;

such aryl radicals can optionally be substituted such as for example the N-substituted pyrrolyl radical, for example N-methylpyrrolyl, the substituted 3- or 4-isoxazolyl radical, for example, 3-aryl-5-methylisoxazol-4-yl, the aryl group being, for example, a phenyl or halophenyl group;

—the terms arylalkyl and arylalkenyl designate radicals in which the alkyl, alkenyl and aryl radicals respectively can take the values defined above for these radicals;

as examples of such arylalkyl radicals the following radicals can be mentioned: benzyl, diphenylmethyl, triphenylmethyl, naphthylmethyl, indenylmethyl, thienylmethyl such as thien-2-yl-methyl, furylmethyl such as furfuryl, pyridylmethyl, pyrimidylmethyl or pyrrolylmethyl, it being understood that in the non-exhaustive list of examples of radicals as mentioned above, the alkyl radical can also be represented by ethyl, propyl or butyl radicals such as, for example, in the phenylethyl radical;

as examples of arylalkenyl radicals, there can be mentioned the examples given above of arylalkyl radicals in which the alkyl radical is replaced by an alkenyl radical such as for example in the phenylvinyl or phenylallyl radicals, it being understood that in these radicals the phenyl radical can also be replaced by a naphthyl, pyridyl radical or also for example one of the aryl radicals as defined above in the non-exhaustive list of aralkyl radicals, —the terms aryloxy and arylthio designate radicals in which the aryl radical can take the values defined above for this radical;

in a non-exhaustive manner examples of such aryloxy and arylthio radicals can be mentioned such as, for example, the phenoxy, naphthyloxy, pyridyloxy, phenylthio and naphthylthio radicals.

In the products of formulae (I) and (IC) and in what follows:

—the terms monocyclic radical and radical constituted by condensed rings designate aryl radicals, or unsaturated carbocyclic or heterocyclic radicals as defined above, but also designate saturated heterocyclic radicals, it being understood that the heterocyclic radicals as defined above can contain one or more heteroatoms chosen from oxygen, nitrogen or sulphur atoms and that when these heterocyclic radicals contain more than one heteroatom, the heteroatoms of these heterocyclic radicals can be identical or different: among the saturated heterocyclic monocyclic radicals, there can be mentioned, for example, the pyrrolidinyl, imidazolidinyl, pyrazolidinyl, piperidyl, piperazinyl or morpholinyl radicals, among the radicals constituted by saturated heterocyclic condensed rings, 1,10-diaza 4-anthryl can for example be mentioned, —the term linear or branched alkylene radical preferably designates the methylene and ethylene radicals but also the n-propylene, isopropylene, n-butylene, isobutylene, sec-butylene and tert-butylene radicals, —the term carbamoyl designates the non-substituted carbamoyl radical or the substituted carbamoyl radical for example as indicated hereafter for

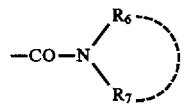

in particular substituted carbamoyl represents for example a lower N-monoalkyl carbamoyl group, such as N-methylcarbamoyl, N-ethylcarbamoyl, a lower N,N-dialkyl carbamoyl group, such as N,N-dimethylcarbamoyl, N,N-diethycarbamoyl; an N-(lower hydroxyalkyl) carbamoyl group, such as N-(hydroxymethyl) carbamoyl, N-(hydroxyethyl) carbamoyl, a lower carbamoylalkyl group, such as carbamoylmethyl, carbamoylethyl.

The amino radicals that can be represented by one or more of the optional substituents of the radicals defined in the products of formulae (I) and (IC) and in what follows and that can be represented by or carried by in particular the radicals:

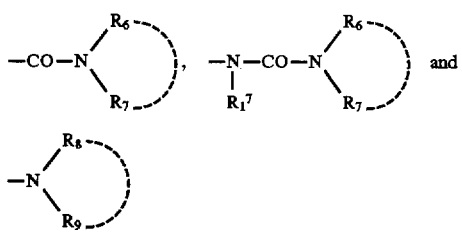

designate radicals in which two identical or different radicals are linked to the nitrogen atom, chosen from the hydrogen atom; alkyl radicals as defined above in order to give preferably the monoalkyl- or dialkylamino radicals in which the linear or branched alkyl radicals contain 1 to 6 carbon atoms and in particular. The following radicals:
methyl, ethyl, isopropyl, trifluoromethyl, pentafluoroethyl, hydroxymethyl, hydroxyethyl, methoxymethyl, methoxyethyl, ethoxyethyl; alkenyl radicals as defined above and preferably represented by the vinyl and allyl radicals; the carbocyclic or heterocyclic aryl or arylalkyl radicals as defined above, and in particular phenyl, tetrazolyl, benzyl, phenethyl, naphthyl, indolyl, indolinyl, thienyl, furyl, pyrrolyl, pyridyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl.

The above radicals represent for example and in a non-exhaustive manner, the NH—aryl radicals such as —NH—tetrazolyl; —NH—alkyl; —N—(alkyl)$_2$; —NH—CO—NH—alkyl such as —NH—CO—NH—tBu; —NH—CO—NH—n-propyl; NH—CO—NH—aryl such as —NH—CO—NH—tetrazolyl or —NH—CO—NH—pyridyl or —N(alkyl)—CO—NH—tetrazolyl, it being understood that in all these radicals, the alkyl and aryl radicals can take the values indicated above for these radicals and optionally be substituted as indicated above for these radicals.

When $R_6$ and $R_7$ on the one hand or $R_8$ and $R_9$ on the other hand form a heterocycle with the nitrogen atom to which they are linked, it may be, for example, one of the following rings: pyrrolyl, imidazolyl, pyridyl, pyrazinyl, pyrimidyl, indolyl, indolinyl, purinyl, quinolyl, pyrrolidinyl, piperidyl, piperidino, morpholino, piperazinyl; these radicals can be optionally substituted by the substituents already mentioned previously and in particular by one or more radicals chosen from chlorine and fluorine atoms, and the following radicals: methyl, ethyl, isopropyl, tert-butyl, methoxy, ethoxy, propoxy, benzoyl, methoxycarbonyl, ethoxycarbonyl, such as for example in methylpiperazinyl, ethylpiperazinyl, propylpiperazinyl, phenylpiperazinyl or benzylpiperazinyl:
in these last two radicals, the phenyl and benzyl radicals can be substituted as indicated previously in the aryl, arylalkyl and arylalkenyl radicals.

The acyl radicals that can be represented by $R_8$ and $R_9$ are as defined previously and can be chosen for example from the acetyl, propionyl, butyryl, valeryl or carbamoyl radicals.

The $Y_1$ and $Y_2$ radicals can represent the values defined above for the monocyclic aryl radicals or the aryl radicals constituted by condensed rings, it being understood that in the case where B represents a single bond, $Y_2$ can also represent a non-cyclized radical such as, for example, a hydrogen atom, a cyano radical or a free, salified or esterified carboxy radical, this esterified carboxy radical preferably designating a lower alkyloxy carbonyl group such as methoxycarbonyl, ethoxycarbonyl or benzyloxycarbonyl.

The $Y_1$ or $Y_2$ radicals, identical or different, can represent an aryl radical optionally substituted by one or more radicals preferably chosen from halogen atoms and the following radicals:

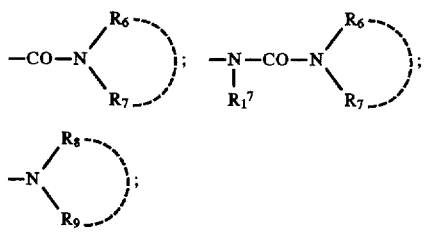

—(CH$_2$)$_{m1}$—S(O)$_{m2}$—Z'—R'$_{14}$; hydroxyl; nitro; tetrazole; isoxazole; alkyl; alkenyl; alkyloxy; acyl and free, salified, esterified or amidified carboxy, these radicals being as defined above and hereafter.

The carboxy radical or radicals of the products formulae (I) and (IC) can be salified, esterified or amidified by various groups known to a man skilled in the art, among which there can be mentioned, for example:
—among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine,
—among the esterification compounds, alkyl radicals to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the following groups: chloromethyl, hydroxypropyl, methoxymethyl, propionyloxymethyl, methylthiomethyl, dimethylaminoethyl, benzyl or phenethyl,
—among the amidification compounds, the following radicals:
—CO$_2$—NH—COOH; —CO$_2$—NH—COO aryl; —CO$_2$—NH—COO alkyl; —CO$_2$—NH—SO$_2$—O alkyl; —CO$_2$—NH—SO$_2$—O aryl; —CO$_2$—NH—SO$_2$—N(alkyl)$_2$; in which the alkyl and aryl radicals have the meanings indicated above for these radicals and are optionally substituted as indicated above, and in particular aryl represents phenyl and optionally salified tetrazolyl.

The addition salts with mineral or organic acids of the products of formulae (I) and (IC) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesutphonic, ethanesulphonic, propanesulphonic, alkyldisulphonic such as for example methanedisulphonic, alpha,beta-ethanedisulphonic, arylmonosulphonic such as benzenesulphonic and aryldisulphonic.

The carboxy radical or radicals of the products of formulae (I) and (IC) can be salified by mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine.

The alkyl, alkenyl and alkynyl radicals as defined above as well as the alkyl or alkenyl radicals of the alkylthio, arylalkyl and arylalkenyl radicals as defined above, can be non-substituted or carry one or more substituents chosen, for example, from the group formed by halogen atoms, such as chloro or bromo, as in, for example, the 2-bromoethyl group; hydroxyl radicals; aryl radicals as defined above, that being a monocyclic radical or a radical constituted by condensed rings, carbocyclic or heterocyclic, it being understood that the heterocyclic radicals as defined above can contain one or more heteroatoms chosen from oxygen, nitrogen or sulphur atoms and that when these heterocyclic radicals contain more than one heteroatom, the heteroatoms of these heterocyclic radicals can be identical or different, this heterocyclic radical being able to be linked by a carbon atom or, if appropriate, by a nitrogen atom; arylalkyl radicals in which the aryl radical is as defined above; cycloalkyl radicals, for example cyclopropyl, cyclopentyl or cyclohexyl; cycloalkenyl radicals such as for example the cyclohexenyl radical can be optionally substituted, among which there can be mentioned 1,3-dimethyl cyclohexene; alkyloxy radicals as defined above for example methoxy, ethoxy, n-propoxy or isopropoxy as in for example the methoxymethyl or 1-ethoxyethyl groups; substituted alkyloxy radicals such as (tri-haloalkyl) oxy such as, for example, trifluoromethoxy; aryloxy radicals, for example phenoxy; (arylalkyl) oxy radicals, for example benzyloxy; mercapto radicals; alkylthio radicals, for example methylthio or ethylthio; substituted alkylthio such as trihaloalkylthio such as, for example, arylthio radicals; aralkylthio radicals; aralkylthio radicals; amino radicals as in, for example, the 2-aminoethyl group; amino radicals substituted by one or two radicals chosen for example from alkyl, alkenyl, aryl and arylalkyl radicals as defined above such as for example monoalkylamino in, for example, methylamino or ethylamino, such as for example dialkylamino in, for example, dimethylamino; nitro radicals; cyano radicals; azido radicals; carboxy radicals; esterified carboxy radical, for example methoxycarbonyl or ethoxycarbonyl; formyl radicals; acyl radicals, for example acetyl, propionyl or benzoyl; acyl radicals substituted for example by an amino radical as defined above or by a cyclic radical linked to the acyl radical by a nitrogen atom, this cyclic radical being able to contain optionally one or more heteroatoms chosen from nitrogen, oxygen or sulphur atoms and as defined above; acyloxy radicals, for example acetoxy or propionyloxy; carbamoyl radicals; substituted carbamoyl radicals, for example a lower N-monoalkyl carbamoyl group, such as N-methylcarbamoyl, N-ethylcarbamoyl, a lower N,N-dialkyl carbamoyl group, such as N,N-dimethylcarbamoyl, N,N-diethylcarbamoyl; an N-(lower hydroxyalkyl) carbamoyl group, such as N-(hydroxymethyl) carbamoyl, N-(hydroxyethyl) carbamoyl, a lower carbamoylalkyl, such as carbamoylmethyl, carbamoylethyl; phthalimido radicals; acylamido radicals, for example acetamido or benzamido; alkoxycarbonylamino radicals, for example methoxycarbonylamino or ethoxycarbonyl; or (arylalkyl) oxycarbonylamino, for example benzyloxycarbonylamino.

The aryl and alkyloxy radicals as defined above and the aryl radicals of the arylalkyl and arylalkenyl radicals as defined above, can be non-substituted or carry one or more substituents chosen, for example, from the list indicated above for the optional substituents of the alkyl, alkenyl and alkynyl radicals as defined above, so as for example to give the o-chlorophenyl radical, but can also be substituted by one or more radicals chosen from the group formed by alkyl radicals, such as lower alkyl, for example methyl, ethyl, or also isopropyl or terbutyl; alkenyl radicals; substituted alkyl radicals such as for example trihaloalkyl as in trifluoromethyl; alkenyl radicals such as, for example, vinyl or allyl; alkynyl radicals such as, for example, propargyl.

The  radicals as defined above can take respectively the same values as those defined for the radicals:

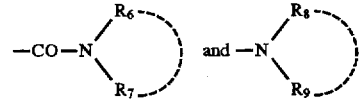

Among the substituents that can be contained by the alkyl, alkenyl, alkynyl, alkyloxy, alkylthio, aryl, arylalkyl and arylalkenyl radicals as defined above, there can be mentioned more particularly halogen atoms, such as chloro and bromo; hydroxyl radicals; acyl radicals such as, for example, acetyl, propionyl, butyryl, valeryl, hexanoyl, acryloyl, crotonoyl or carbamoyl; benzoyl radicals; esterified carboxy preferably designating a lower alkyloxy carbonyl group such as methoxycarbonyl, ethoxycarbonyl or benzyloxycarbonyl; alkyl radicals such as methyl or ethyl; amino radicals; substituted amino radicals, such as monoalkyl- and dialkylamino radicals, for example methylamino, ethylamino or dimethylamino; alkyloxy radicals, for example methoxy, ethoxy or isopropoxy; aryl radicals such as phenyl, biphenyl, naphthyl, indenyl, indolyl or indolinyl; aralkyl radicals such as, for example, benzyl or phenethyl; the alkyl, alkyloxy and aryl radicals as defined above being able themselves to be substituted by one or more identical or different radicals, chosen, for example, from the group formed by the following radicals: hydroxy, linear or branched alkyl and alkyloxy, for example methyl, ethyl, tert-butyl, methoxy, ethoxy, isopropoxy; substituted amino, such as mono- alkyl- and dialkylamino, for example methylamino, ethylamino radicals containing 6 links such as phenyl, pyrannyl, pyridyl pyrimidinyl pyridazinyl, pyrazinyl, piperidyl piperazinyl, piperidino and morpholino radicals; carbocyclic or heterocyclic monocyclic radicals containing 5 links, such as for example one of the following radicals: furyl, pyrrolyl, pyrrolinyl, imidazolyl or pyrazolyl, isothiazolyl, isoxazolyl, pyrrolidinyl, imidazolidinyl, pyrazolidinyl; carbocyclic or heterocyclic radicals constituted by condensed rings among which for example naphthyl, indolyl, quinolyl purinyl radicals as well as their isomers of position of the heteroatom or heteroatoms, for example of nitrogen, such as for example the indazolyl or isoquinolyl radical.

When such heterocyclic radicals contain one or more nitrogen atoms, this or these nitrogen atoms can be non-substituted or one or more of these nitrogen atoms can be substituted, for example, by a linear or branched alkyl or alkyloxy radical containing 1 to 5 carbon atoms, as defined above, for example methyl, ethyl, isopropyl, tert-butyl, methoxy or ethoxy, a phenyl or benzyl radical, these radicals being able themselves to be substituted by the substituents already mentioned above for the aryl and arylalkyl radicals: there can be mentioned, as examples, methylpiperazinyl, ethylpiperazinyl, propylpiperazinyl, phenylpiperazinyl or benzylpiperazinyl radicals.

Among the particularly preferred values of such radicals, there can be mention in particular the phenyl, naphthyl, pyridyl, piperazinyl, pyrimidinyl, pyridazinyl and pyrazinyl radicals.

A particular subject of the invention is the products of formulae (I) and (IC) as defined above, in which:
$R_1$, $R_2$, $R_3$ and $R_4$, identical or different, are chosen from the group formed by:
— the hydrogen atom, halogen atoms,
— mercapto, alkylthio, phenylthio radicals,
— linear or branched alkyl and alkenyl radical containing at most 6 carbon atoms and optionally substituted by one or more identical or different substituents chosen from halogen atoms, the hydroxyl radical, alkoxy radicals containing 1 to 4 carbon atoms, alkylthio, phenylthio, pyridylthio radicals, in which the alkyl radical contains 1 to 4 carbon atoms and the sulphur atom is optionally oxidized in the form of the sulphoxide or sulphone, the following radicals: amino, mono- and dialkylamino, pyrrolidinyl morpholinyl piperidinyl phenyl, benzyl, benzyloxy and phenoxy,
— the carboxy radical, free salified or esterified by a linear or branched alkyl radical containing at most 4 carbon atoms, optionally substituted as indicated above,
— the phenyl, pyridyl, pyrrolidinyl radical,
— the pyrrolidinyl-carbonyl, morpholinyl-carbonyle, carbamoyl, dialkylcarbamoyl, piperidyhyl-carbonyl radical, $R_5$ represents a methylene radical, Y represents a phenyl or biphenyl radical optionally substituted by one or more radicals chosen from cyano, free, salified, esterified or amidified carboxy, tetrazolyl, isoxazolyl radicals and the $-SO_2-ZC-R_{14}C$ radical in which ZC represents the —NH—, —NH13 CO—, —NH—$CO_2$—, —NH—CO—NH— radicals or a single bond and $R_{14}C$ represents one of the following radicals: methyl, ethyl, propyl, vinyl, allyl, pyridyl, phenyl, benzyl, pyridylmethyl, pyridylethyl, nitropyridyl, pyrimidyl, tetrazolyl, diazolyl, piperidinyl, alkylpiperidinyl, thiazolyl, alkylthiazolyl, tetrahydrofuranyl, methyltetrahydrofuranyl;
the said products of formulae (I) and (IC) being in all the possible racemic, enantiomeric and diastereoisomeric isomer forms, as well as the addition salts with mineral and organic acids or with mineral and organic bases, of the said products of formulae (I) and (IC).

A more particular subject of the invention is the products of formulae (I) and (IC) as defined above, in which: $R_1$, $R_2$, $R_3$ and $R_4$, identical or different, are chosen from the group formed by:
— the hydrogen atom,
— linear or branched alkyl radicals containing at most 4 identical or different substituents chosen from halogen identical or different substituents chosen from halogen atoms, the hydroxyl radical, or the following radicals: amino, mono- and dialkylamino, pyrrolidinyl, morpholinyl, piperidinyl, benzyl, benzyloxy and phenoxy,
— the carboxy radical, free, salified, esterified or amidified by a linear or branched alkyl radical containing at most 4 carbon atoms,
— the following radicals: pyrrolidinyl-carbonyl, morpholinylcarbonyl, carbamoyl, dialkylcarbamoyl, piperidynyl-carbonyl, $R_5$ represents a methylene radical, Y represents a phenyl or biphenyl radical optionally substituted by one or more radicals chosen from the following radicals: cyano, free, salified, esterified or amidified carboxy, tetrazolyl, isoxazolyl and $-SO_2-ZC-R_{14}C$ in which ZC represents the —NH—, —NH—CO—, —NH—$CO_2$—, —NH—CO—NH— radicals or a single bond and $R_{14}C$ represents one of the following radicals: methyl, ethyl, propyl, vinyl, allyl, pyridyl, phenyl, benzyl, pyridylmethyl, pyridylethyl, nitropyridyl, pyrimidyl, tetrazolyl, diazolyl, piperidinyl, alkylpiperidinyl, thiazolyl, alkylthiazolyl, tetrahydrofuranyl, methyltetrahydrofuranyl;

the said products of formulae (I) and (IC) being in all the possible racemic, enantiomeric and diastereoisomeric isomer forms, as well as the addition salts with mineral and organic acids or with mineral and organic bases, of the said products of formulae (I) and (IC).

The $-(CH_2)_{m1}-S(O)_{m2}-Z'-R'_{14}$ radical can represent for example the radicals in which $(CH_2)_{m1}$ represents the values of the alkylene radicals such as, for example, methylene, ethylene, n-propylene or n-butylene and $R'_{14}$ can represent an alkyl or alkenyl radical chosen from the values defined above or an aryl radical also chosen from the values indicated above such as for example phenyl, pyridyl, biphenyl, naphthyl, tetrazolyl; the alkyl or alkenyl radical that can be represented by the $R'_{14}$ radical can optionally be substituted by an aryl radical chosen from the values defined above to form an aralkyl or aralkenyl radical.

These alkyl, alkenyl, aryl, aralkyl and arylalkenyl radicals can be substituted themselves as indicated above for these radicals.

The following radials can be mentioned by way of example and in a non-exhaustive manner:
$-CH_2-SO_2-NH_2$, $-CH_2-SO_2-NH-C_6H_5$, $-SO_2-NH-CO-NH-CH_3-$, $-SO_2-NH-CO-NH-C_6H_5$, $-SO_2-NH-CO-NH-CF_3-$, $-SO_2-NH-CO-NH-alkyl$, $-SO_2-NH-CO-NH-nPr$, $-SO_2-NH-CO-NH-tBu$, $-SO_2-NH-CO-NH-CH_2-C_6H_5$, $-SO_2-NH-CO-NH-C_6H_5-Cl$, $-SO_2-NH-CO-NH-aryl$, $-SO_2-NH-CO-NH-tetrazolyl$

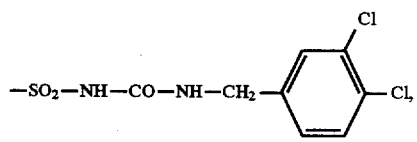

$-SO_2-NH-CO-NH-CH=CH-CH_3$, $-SO_2-NH-CO-NH-CH_2-\underset{A}{C}=\underset{B}{CH}$ in which A and B, identical or different, are chosen from the hydrogen atom, phenyl, pyridyl and pyrimidyl radicals;

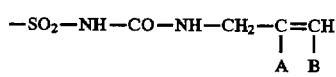

$-SO_2-NH-tetrazolyl$

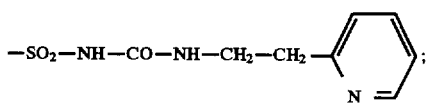

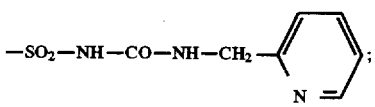

-continued

—SO₂—NH—CO—NH—CH₂ ; 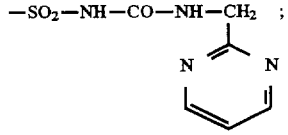

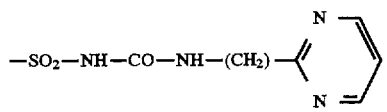

—SO₂—NH—SO₂—tetrazolyl;
—SO₂—NH—SO₂—NH₂;
—SO₂—NH—SO₂—NH(tBu);
—SO₂—NH—SO₂—tBu;
and also, as non-exhaustive examples, —NH—(alkyl), NH-aryl, —NH-tetrazolyl, —SO₂—NH—CO₂—alkyl, —SO₂—NH—CO₂—C₂H₅, —SO₂—NH—CO₂—aryl, —SO₂—NH—CO₂—tetrazolyl, SO₂—NH—CO—alkyl, —SO₂—NH—CO—nPr, —NH—CO—NH—aryl, —NH—CO—NH—tetrazolyl, —CO₂—NH—CO₂—aryl, —CO₂—NH—CO₂—tetrazolyl, —CO₂—SO₂—O—aryl, —CO₂—NH—SO₂—N(alk)₂;

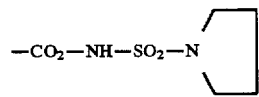

The aryl radical that is represented by $Y_1$ can be substituted by one or more radicals chosen from the values of $R_2$ and $R_3$ and in particular by the —NH—(CH₂)$_m$—Z—R₁₄ and —CO—NH—(CH₂)$_m$SO₂—Z—R₁₄ radicals in which the (CH₂)$_m$SO₂—Z—R₁₄ radical can take for example the values indicated above.

The following radicals can be mentioned by way of example and in a non-exhaustive manner:
—NH—SO₂—CH₃, —NH—SO₂—C₆H₅, —NH—SO₂—CF₃, —NH—CH₂—SO₂—NH—C₆H₅, —CO—NH—SO₂—C₂H₅, —CO—NH—SO₂—CH₃, —CO—NH—SO₂—CH₂—C₆H₅.

Among the products which are a subject of the invention, there can be mentioned quite particularly, the product of formula (I) corresponding to the following definition:
—1-(benzyl) 2-(benzyloxymethyl) 5-(methyl) 3-(phenylthio) 4-pyridone.

Also a subject of the invention is a preparation process for the products of formula (I) as defined above, characterized in that:
a product of formula (II):

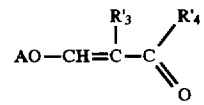 (II)

in which $R'_3$ and $R'_4$ have the meanings indicated above for $R_3$ and $R_4$ respectively in which the optional reactive functions are optionally protected by protective groups and A represents an acyl group, is reacted with a product of formula (III):

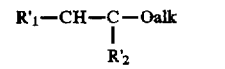 (III)

in which $R'_1$ and $R'_2$ have the meanings indicated above for $R_1$ and $R_4$ respectively in which the optional reactive functions are optionally protected by protective groups and alk represents an alkyl radical containing at most 5 carbon atoms, in order to obtain the products of formula (IV):

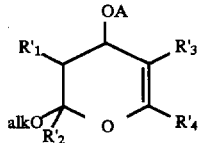 (IV)

in which $R'_1$, $R'_2$, $R'_3$, $R'_4$ A and alk have the meanings indicated above, which are saponified in order to obtain the products of formula (V):

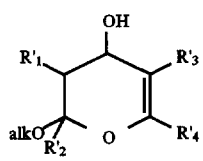 (V)

in which $R'_1$, $R'_2$, $R'_3$, $R'_4$ and alk have the meanings indicated above,
which are oxidized in order to obtain the products of formula (VI):

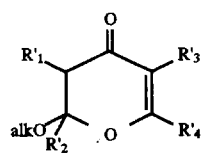 (VI)

in which $R'_1$, $R'_2$, $R'_3$, $R'_4$ and alk have the meanings indicated above, which are subjected to an elimination reaction of the alkyloxy function in order to obtain the products of formula (VII):

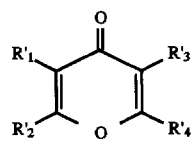 (VII)

in which $R'_1$, $R'_2$, $R'_3$, $R'_4$ have the meanings indicated above, which are reacted with a product of formula (VIII):

NH₂—R₅—Y' (VIII)

in which R₅ has the meaning indicated above and Y' has the meaning indicated above for Y in which the optional reactive functions are optionally protected by protective groups in order to obtain a product of formula (IX):

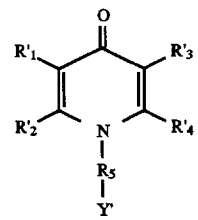 (IX)

in which $R'_1$, $R'_2$, $R'_3$, $R_5$ and Y' have the meanings indicated above, which product of formula (IX) is subjected, if desired and if necessary, to one or more of the following reactions, in any order:
— an elimination reaction of the protective groups that can be carried by the protected reactive functions,
— a salification reaction by a mineral or organic acid or by a mineral or organic base in order to obtain the corresponding salt, —an esterification reaction of the acid function, —a saponification reaction of the ester function into an acid function, —a conversion reaction of the alkyloxy function into a hydroxyl function, —a conversion reaction of the cyano function into an acid function, —a reduction reaction of the carboxy function into an alcohol function, —a resolution reaction of the racemic forms, the said products of formula (I) thus obtained being in all the possible racemic, enantiomeric and diastereoisomeric isomer forms.

In the preferred conditions for implementing the invention, the above preparation process for the products of formula (I) can be carried out in the following manner: the product of formula (IV) can be obtained by reacting an ether such as for example an alkylalkenylether of formula (III) on the oxo function of the product of formula (II) for example in the presence of a solvent such as for example hydroquinone at a temperature of about 80° to 100° C., for about 24 hours.

The saponification reaction of the product of formula (IV) thus formed into a product of formula (V) can be carried out for example at ambient temperature in a solvent such as for example an alcohol like for example methanol or ethanol in the presence of salts such as for example sodium or potassium bicarbonate or a sodium alcoholate, at a temperature of about 100° to 250° C.

The product of formula (VI) can be obtained by oxidation of the product of formula (V) for example in the presence of pyridinium dichromate or pyridinium chlorochromate in a solvent such as for example dimethylformamide or dichloromethane.

The elimination reaction of the alkyloxy function of the product of formula (VI) to obtain the product of formula (VII) can be carried out for example in the presence of an acid such as paratoluene sulphonic acid or camphosulphonic acid, in a solvent such as for example toluene.

The addition reaction of the products of formula (VIII) on the products of formula (VII) thus obtained can be carried out in the usual conditions known to a man skilled in the art and for example in a solvent such as methanol, ethanol, ethoxy ethanol, methoxy ethanol.

According to the values of $R'_1$, $R'_3$, $R'_4$, and $Y'$, the products of formula (IX) thus obtained constitute or do not constitute the products of formula (I).

The products of formula (IX) thus obtained, in particular to give the products of formula (I), can be subjected, if desired and if necessary, to one or more of the reactions indicated above.

The various reactive functions that can be carried by certain compounds of the reactions defined above can, if necessary, be protected: it may be for example the hydroxyl, acyl, free carboxy or also amino and monoalkylamino radicals that can be protected by appropriate protective groups.

The following non-exhaustive list of examples of the protection of the reactive functions can be mentioned:

—the hydroxyl groups can be protected for example by alkyl radicals such as tert-butyl, trialkylsilyl, dihydropyran, methoxymethyl or tetrahydropyrannyl, —the amino groups can be protected for example by acetyl, trityl, benzyl, tert-butoxycarbonyl, phthalimido radicals or other radicals known in the chemistry of the peptides, —the acyl groups such as the formyl group can be protected for example in the form of cyclic or noncyclic ketals such as dimethyl- or diethylketal or ethylene dioxyketal, —the acid functions of the products described above can be, if desired, amidified by a primary or secondary amine for example in methylene chloride in the presence of 1-ethyl-3-(dimethylaminopropyl) carbodiimide hydrochloride at ambient temperature, —the acid functions can be protected for example in the form of esters formed with easily cleavable esters such as benzyl or terbutyl esters or esters known in the chemistry of the peptides.

The elimination of these protective groups is carried out in the usual conditions known to a man skilled in the art, notably acid hydrolysis carried out with an acid such as one of the following acids: hydrochloric, benzene sulphonic or para-toluene sulphonic, formic or trifluoroacetic.

The phthalimido group is eliminated by hydrazine.

A list of the different protective groups which can be used will be found for example in the Patent BF 2,499,995.

The products described above can, if desired, be subjected to salification reactions by a mineral or organic acid or by a mineral or organic case, in particular on the optional carboxy functions, these reactions being able to be carried out according to the usual methods known to a man skilled in the art.

The products described above can, if desired, be subjected, on the optional carboxy functions, to esterification reactions that can be carried out according to the usual methods known to a man skilled in the art.

The optional esters functions of the products described above can be, if desired, saponified into an acid function, these saponification reactions being able to be carried out in the usual conditions known to a man skilled in the art, notably by acid or alkaline hydrolysis for example by soda or potash in an alcoholic medium such as, for example, in methanol or also by hydrochloric or sulphuric acid.

The optional alkyloxy functions such as in particular methoxy of the products described above can be, if desired, converted into a hydroxyl function in the usual conditions known to a man skilled in the art, for example by boron tribromide in a solvent such as for example methylene chloride, by pyridine hydrobromide or hydrochloride or also by hydrobromic or hydrochloric acid in water or acetic acid under reflux.

The optional cyano functions of the products described above can be, if desired, converted into an acid function in the usual conditions known to a man skilled in the art, for example by a double hydrolysis carried out in an acid medium such as for example in a mixture of sulphuric acid, glacial acetic acid and water, these three compounds being preferably in equal proportions, or also in a mixture of soda, ethanol and water under reflux.

The optional carboxy or esterified carboxy functions of the products described above can, if desired, be reduced into an alcohol function by methods known to a man skilled in the art and notably by lithium aluminium hydride in a solvent such as for example tetrahydrofuran or also dioxan or ethyl ether.

The optional optically active forms of the products of formula (I) can be prepared by resolution of the racemics according to the usual methods.

The compounds of formulae (I) and (IC) as defined above as well as their addition salts with acids have useful pharmacological properties.

The products are endowed with antagonistic properties for the angiotensin II receptor and are thus in particular inhibitors of the effects of angiotensin II, especially of the vasoconstrictive effect and also of the trophic effect at the level of the myocytes.

Certain products of the present invention also possess antagonistic properties for the endothelin receptor and are thus notably antagonists of the vasoconstrictive effect of endothelin.

The compounds of formulae (I) and (IC) also possess the property of improving the cognitive functions.

These properties justify their use in therapeutics and a subject of the invention is also, as medicaments, the products as defined by formula (I) above, the said products of formula (I) being in all the possible racemic or optically active isomer forms, as well as the addition salts with pharmaceutically acceptable mineral or organic acids or mineral and organic bases of the said products of formula (I).

A particular subject of the invention is, as medicaments, the products of formula (I) as defined above and corresponding to formula (IC):

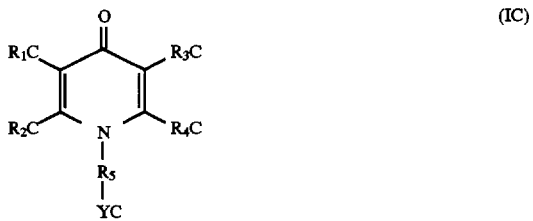

(IC)

in which $R_1C$, $R_2C$, $R_3C$ and $R_4C$, identical or different, are chosen from the group formed by:
— the hydrogen atom,
— halogen atoms,
— the hydroxyl radical,
— the following radicals: mercapto, cyano, nitro, formyl, benzoyl, acyl having at most 6 carbon atoms, sulpho, carboxy radicals, free, salified or esterified by a linear or branched alkyl radical containing at most 4 carbon atoms, tetrazole radicals,
— the following radicals: linear or branched alkyl, cycloalkyl, alkenyl, alkyloxy and alkylthio containing at most 6 carbon atoms, phenyl, naphthyl, benzyl and phenylthio, all these radicals being optionally substituted by one or more identical or different radicals chosen from halogen atoms, the hydroxyl radical, alkyloxy and alkylthio radicals containing at most 4 carbon atoms, these radicals being optionally substituted by an amino, mono- or dialkylamino radical in which the alkyl radical contains 1 to 4 carbon atoms, trifluoromethyl, cyano, free, salified or esterified carboxy, benzyloxy, phenoxy; benzylthio, phenylthio and pyridinethio in which the sulphur atom can be oxidized in the form of sulphoxide or sulphone, tetrazole, isoxazole, pyrrolidinyl, pyrrolidinylcarbonyl and phenyl optionally substituted by one or more radicals chosen from halogen atoms, the hydroxyl radical, alkyl and alkoxy radicals containing at most 4 carbon atoms,
— the following radicals: amino, mono- or dialkylamino in which the alkyl radical contains 1 to 4 carbon atoms, carbamoyl, pyrrolyl, pyrrolidinyl, morpholino, piperazinyl, pyrrolylmethyl, morpholinomethyl, piperazinylmethyl, pyrrolylcarbonyl, morpholinocarbonyl, pyrrolidinylcarbonyl, piperazinylcarbonyl, all the piperazinyl radicals being optionally substituted on the second nitrogen atom by an alkyl or phenyl radical, these alkyl and phenyl radicals being themselves optionally substituted by one or more radicals chosen from halogen atoms, the hydroxyl radical, nitro, alkyl or alkyloxy radicals containing at most 4 carbon atoms, trifluoromethyl, cyano, free, salified or esterified carboxy, tetrazolyl and isoxazolyl radicals, $R_5$ represents a linear or branched divalent alkylene radical, containing at most 4 carbon atoms, YC represents a phenyl or biphenyl radical optionally substituted by one or more radicals chosen from the following radicals: hydroxyl; halogen; alkyl, alkenyl and alkyloxy containing at most 4 carbon atoms and optionally substituted by a free, esterified or salified carboxy radical; trifluoromethyl; cyano; nitro; free, salified or esterified carboxy; tetrazole optionally protected by a triphenylmethyl radical; isoxazole;
— the —$(CH_2)_p$—$SO_2$—ZC—$R_{14}C$ radical in which P represents the values 0 and 1, ZC represents the —NH—, —NH—CO—, —NH—$CO_2$, —NH—CO—NH— radicals or a single bond and $R_{14}C$ represents one of the following radicals: methyl, ethyl, propyl, vinyl, allyl, pyridyl, phenyl, benzyl, pyridylmethyl, pyridylethyl, nitro-pyridyl, pyrimidyl, tetrazolyl, diazolyl, piperidinyl, alkylpiperidinyl, thiazolyl, alkylthiazolyl, tetrahydrofuranyl, methyltetrahydrofuranyl; amino or carbamoyl optionally substituted by one or two radicals chosen from the —$(CH_2)_p$—$SO_2$—ZC—$R_{14}C$ radicals as defined above and the alkyl and alkenyl radicals containing at most 4 carbon atoms and optionally substituted;

all these radicals being optionally substituted by one or more radicals chosen from halogen atoms, the following radicals: hydroxyl, alkyl and alkenyl, alkoxy containing at most 4 carbon atoms, trifluoromethyl, cyano, free, salified or esterified carboxy or tetrazolyl;

the said products of formula (IC) being in all the possible racemic, enantiomeric and diastereoisomeric isomer forms, as well as the addition salts with pharmaceutically acceptable mineral and organic acids or mineral and organic bases of the said products of formula (IC).

A more particular subject of the invention is, as medicaments, the products described hereafter in the examples and in particular:
—(1_(benzyl) 2-(benzyloxymethyl) 5-(methyl) 3-(phenylthio) 4-(pyridone,
as well as its addition salts with pharmaceutically acceptable mineral or organic acids or mineral or organic bases.

The medicaments which are a subject of the invention can be used in the treatment of cardiovascular illnesses presenting an alteration of vasomotricity: myocardial infarction, cardiac insufficiency, renal insufficiency, angina of the chest, cerebral vascular spasm, Raynaud's disease, arterial hypertension and all illnesses following an ischemia. These medicaments, which are a subject of the invention, could also be used for the treatment of glaucoma, atherosclerosis, asthma and different types of visceral spasms, and also as neuronal protective substances or also in the prevention of post-angioplastic recurrence of stenosis.

They can also be used in the treatment of certain gastrointestinal and gynaecological disorders and in particular for a relaxing effect at the level of the uterus.

The medicaments which are a subject of the invention can also be used in the treatment of disorders of the memory and the cognitive functions, anxiety, depression, senile dementia and Alzheimer's disease.

The invention extends to pharmaceutical compositions containing as active ingredient at least one of the medicaments as defined above.

These pharmaceutical compositions can be administered by buccal, rectal, or parenteral route or by local route as a topical application on the skin and mucous membranes.

These compositions can be solid or liquid and be presented in all the pharmaceutical forms commonly used in human medicine such as, for example, plain or sugar-coated tablets, capsules, granules, suppositories, injectable preparations, ointments, creams, gels and aerosol preparations; they are prepared according to the usual methods. The active ingredient can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, preservatives.

The usual dose, variable according to the product used, the patient being treated and the illness in question, can be, for example, from 1 to 100 mg per day for an adult, by oral route.

The starting compounds of formulae (II), (III) and (VIII) can be prepared as indicated hereafter.

To prepare a product of formula (II) as defined above, a compound of formula (IIa):

in which Hal represents a halogen atom and R'$_4$ has the meaning indicated above,
can for example be reacted with a compound of formula (x1):

in which R'$_3$ has the meaning indicated above, in order to obtain a compound of formula (IIb):

in which R'$_3$ and R'$_4$ have the meanings indicated above, which is oxidized into a compound of formula (IIc):

in which R'$_3$ and R'$_4$ have the meanings indicated above, which is reacted with a compound of formula (x2):

in which alk$_1$, alk$_2$, alk$_3$ and alk$_4$, identical or different, represent an alkyl radical containing 1 to 5 carbon atoms, in order to obtain a compound of formula (IId):

in which R'$_3$, R'$_4$ and alk have the meanings indicated above, which is converted into a compound of formula (IIe):

in which R'$_3$ and R'$_4$ have the meanings indicated above, which is reacted with a compound of formula (x3):

in which Hal represents a halogen atom and Ac represents an acyl radical,
in order to obtain the product of formula (II) as defined above.

In the compounds of formulae (IIa) and (x3), Hal can notably represent a chlorine atom.

The experimental conditions of such a preparation of a compound of formula (II) can for example be those indicated in the experimental part of the preparation of Example 1. Examples of such compounds of formulae (II) and (III) are mentioned in particular in the publications whose references are as follows:

—Liebigs Ann. Chem. 1985 pp 2261–2284, M. MAIER, R. R. SCHMIDT

—Chem. Ber. 120, 1987, pp 1505–150 G. HAACZEINO, M. E. MAIER, R. R. SCHMIDT.

Among the compounds of formula (III) that are commercially available, there can be mentioned for example ethyl vinyl ether and ethyl propenyl ether.

Among the examples of the preparation of such compounds of formula (III) described in the literature, the following references can be mentioned in particular:

—P. G. Gassmann, S. J. Purns, J. Org. Chem. 1988, 53, 5574–76,

—A. Ferwanah, W. Presoler, C. Reichardt Tet. Lett. 1973, 3979,

—W. Schmidt, P. Grafen, Liebigs Annal. Chem. 1962, 656, 97,

—G. Wittig, Boll, Krück, Chem. Ber. 1962, 95, 2520,

—J. L. E. Erickson, M. Z. Woskow, J. Org. Chem. 1958, 23, 670,

—J. M. Vatele, Tet, Lett. 1984, 25, 5997–6000,

—C. Earnshow, C. J. Wallis, S. Warren, J. C. S. Perkin Trans. I 1979, 3099–3106.

Examples of the preparation of compounds of formula (VIII) are described in the literature and examples of them are given in particular in U.S. Pat. No. 4,880,804 or EP 0,253,310.

A preparation process of some of the products of formula (VIII) as defined above can consist of subjecting methyl iodobenzoate to the action of iodotoluene, the reaction being carried out for example in the presence of powdered copper at temperature of about 100° C. to 300° C., in order to obtain a product of formula (a):

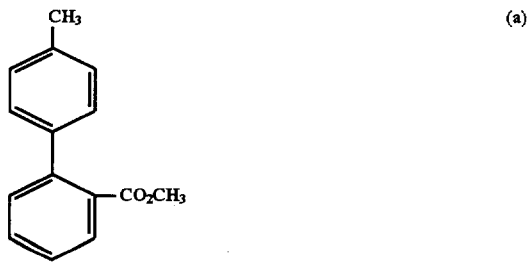

the esterified carboxy radical of which can, if desired, be freed from the alkyl radical by standard methods known to a man skilled in the art or indicated above, for example acid or alkaline hydrolysis, the esterified carboxy radical or the free carboxy radical obtained after liberation of the alkyl radical being able to be subjected to reduction, addition or substitution reactions in any order, these reactions being able to be carried out for example according to standard methods known to a man skilled in the art, which product of formula (a) can be subjected to a bromination reaction on the methyl radical by standard methods known to a man skilled in the art, for example by the action of n-bromosuccinimide in carbon tetrachloride, then to an addition reaction of the amine function in the conditions indicated in the reference U. Ragnarsson, L. Grehn, Acc. Chem. Res. 1991, 24, 285–89 and those references already mentioned, so as to obtain, from the product of formula (a) indicated above, compounds of formula (VIII) as defined above.

Among the compounds of formula (VIII) that are commercially available, there can be mentioned for example benzylamine, 4-aminomethyl benzoic acid, 2-bromobenzylamine, 4-(aminomethyl) benzine sulphonamide, 2-chlorobenzylamine or alpha-amino p-tolunitrile.

By operating in the same manner as described previously, starting with products of formula

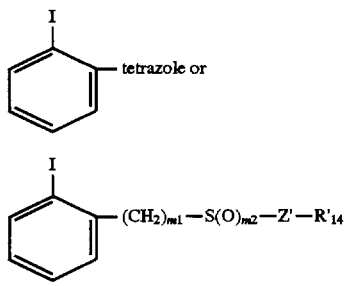

the corresponding products of formula (VIII) can be prepared. The other products of formula (VIII) can also be prepared according to similar methods.

Also a subject of the present invention is, as new industrial products and notably as intermediate products necessary for the preparation of the products of formulae (I) and (IC), the compounds of formulae (IV), (V), (VI) and The following examples illustrate the invention without however limiting it.

The product of formula (II) used at the start of Example was prepared in the following manner:

Preparation of Example 1: 4-acetoxy 1-benzyloxy 3-phenylthio 3-butene 2-one

STAGE A: 2-hydroxy 3-chloro 1-benzyloxypropane

—15.7 ml of 1-chloro 2-epoxypropane
—41.4 ml of benzyl alcohol
—0.2 ml of tin tetrachloride are introduced and the mixture is left to return to ambient temperature then heated to a temperature of about 104° C. for about 3 hours.

The mixture is left to return to ambient temperature, diluted with toluene, water is added, filtration is carried out, the organic phase is washed with sodium carbonate then again with water until a pH of 7 is obtained.

After drying and filtering, the toluene is eliminated, followed by distillation and 26.165 g of expected product is obtained (B.p. 158°–159° C. under 16 mm/Hg).

Analyses:

IR Spectrum (CHCl$_3$)
—OH complex 3598 cm$^{-1}$
aromatic 1498 cm$^{-1}$

STAGE B: 1-benzyloxy 3-phenylthio 2-propanol 25 ml of methanol is introduced, 1.5 g of sodium is added, the mixture is agitated then cooled down to a temperature of about 0° C. and the following are added:

—7.3 ml of thiophenol then—13 g of the product obtained above in Stage A and—5 ml of methanol.

The resultant mixture is heated for 12 hours under reflux at 68° C. then left to return to ambient temperature.

Dilution is carried out with water, followed by extracting 3 times with ether, the ether phase is washed with a saturated aqueous solution of sodium chloride, dried, filtered, the ether is eliminated and 18 g of expected product is obtained.

Analyses

IR Spectrum (CHCl$_3$)
—OH complex 3558 cm$^{-1}$
phenyl-C- 1498 cm$^{-1}$
phenyl-S- 1588 cm$^{-1}$ STAGE C: 1-benzyloxy 3-phenylthio 2-propanone —31.6 g of the product obtained above in Stage B
—215 ml of acetic anhydride and—325 ml of dimethylsulphoxide are introduced and the mixture is agitated at ambient temperature for 24 hours then treated under a nitrogen current in order to eliminate the dimethyl sulphide.

After concentrating, taking up with water, and extracting with ether, the organic phase is washed with a saturated aqueous solution of sodium chloride, dried, filtered, and the ether is eliminated.

After chromatography on silica (hexane: 90/ethyl acetate: 10), 22.9 g of expected product is obtained.

Analyses:

| IR Spectrum (CHCl$_3$) | |
| --- | --- |
| C=O | 1725 cm$^{-1}$ |
| aromatics | 1583 cm$^{-1}$ |
|  | 1495 cm$^{-1}$ |
|  | 1483 cm$^{-1}$ |

STAGE D: 1-benzyloxy 4-dimethylamino 3-phenylthio 3-butene 2-one

—21.24 g of the product obtained above in Stage c) and—12.1 ml of dimethylacetal dimethylformamide are introduced and agitation is carried out for one hour 30 minutes at 70° C., the mixture is left to return to ambient temperature, evaporated to dryness and 24.8 g of expected product is obtained.

Analyses:

| IR Spectrum (CHCl$_3$) | |
| --- | --- |
| conjugated system | 1655 cm$^{-1}$ |
|  | 1580 cm$^{-1}$ |
| aromatics | 1496 cm$^{-1}$ |

STAGE E: 4-benzyloxy 3-oxo 2-(phenylthio) butanal 24.6 g of the product obtained above in Stage d) is introduced into 85 ml of a solution constituted by 6 g of soda, 20 ml of water and 80 ml of ethanol and the whole is heated to a temperature of about 60° C.

The mixture is left to return to ambient temperature and poured into a mixture of 150 ml of ice and 16 ml of pure hydrochloric acid.

Extraction is carried out with 180 ml of ethyl acetate then with 2 lots of 100 ml of ethyl acetate, the organic phase is washed with a saturated aqueous solution of sodium chloride, dried, filtered, concentrated and 22.5 g of expected product is obtained.

Analyses:

| IR Spectrum (CHCl$_3$) | |
|---|---|
| conjugated system | 1633 cm$^{-1}$ |
| | 1609 cm$^{-1}$ |
| aromatics | 1492 cm$^{-1}$ |

STAGE F: 4-acetoxy 1-benzyloxy 3-phenylthio 3-butene 2-one

—2.28 g of the product obtained above in Stage E
—0.65 ml of pyridine and—8 ml of toluene are introduced, the mixture is cooled down to −10° C., 0.57 ml of acetyl chloride in 2 ml of tolune is added and agitation is carried out for about 3 hours at −10° C.

After filtering and washing with toluene, the organic phase is washed with a saturated aqueous solution of sodium chloride, filtered, dried, the toluene is eliminated and 3.3 g of expected product is obtained.

Analyses:

| IR Spectrum (CHCl$_3$) | |
|---|---|
| C=O | 1783 cm$^{-1}$ |
| | 1702 cm$^{-1}$ |
| C=C and | 1598 cm$^{-1}$ |
| aromatics | 1587 cm$^{-1}$ |
| | 1496 cm$^{-1}$ |

EXAMPLE 1: (1-benzyl) (2-benzyloxymethyl) (5-methyl) (3-phenylthio) 4-pyridone

STAGE A: (4-acetoxy) (2-benzyloxymethyl) (6-ethoxy) (5-methyl) (3-phenylthio) 4H(5,6)-pyran —3 g of the product obtained in Stage F of the preparation of Example 1
—16.5 ml of 1-ethylpropenylether and—33 mg of hydroquinone are introduced and heated to a temperature of about 85° C. for about 24 hours.

The mixture is left to return to ambient temperature, concentrated and 5.7 g of a brown oil is obtained containing the expected product. The crude product is purified by chromatography on a silica column (eluant: hexane—ethyl acetate 9-1).

Analyses:

| IR Spectrum (CHCl$_3$) | |
|---|---|
| OAc | 1734 cm$^{-1}$ |
| C=C | 1625 cm$^{-1}$ |
| aromatic | 1586-1497 cm$^{-1}$ |

STAGE B: (2-benzyloxymethyl) (4-hydroxy) (6-ethoxy) (5-methyl) (3-phenylthio) 4H(5,6)-pyran —4.6 g of the product obtained above in Stage a)
—1.417 g of sodium carbonate and—50 ml of methanol are introduced and the mixture is agitated in the presence of a catalytic quantity of sodium methylate at ambient temperature for 16 hours.

Dilution is carried out with water, the organic fraction is washed with a saturated aqueous solution of ammonium chloride, extraction is carried out with ether, the organic phase is dried, filtered, concentrated and 3.23 g of expected product is obtained in the form of a brown oil.

Analyses:

| IR Spectrum (CHCl$_3$) | |
|---|---|
| OH | 3540 cm$^{-1}$ |
| heterocycle and | 1627 cm$^{-1}$ |
| aromatic | 1602 cm$^{-1}$–1583 cm$^{-1}$ |
| | 1496 cm$^{-1}$–1478 cm$^{-1}$ |

STAGE C: (2-benzyloxymethyl) (6-ethoxy) (5-methyl) (3-phenylthio) 4-dihydropyrone —310 mg of the product obtained above in Stage B
—910 mg of pyridinium dichromate and—5 ml of dimethylformamide are introduced and agitation is carried out at ambient temperature for about 3 hours.

The mixture is diluted with water, extracted with ether, filtered, the organic phase is dried, filtration is carried out again followed by concentration, and 477 mg of expected product is obtained in the form of a yellow oil.

Analyses:

| IR Spectrum (CHCl$_3$) | |
|---|---|
| C=O | 1684 cm$^{-1}$ |
| heterocycle and | 1582 cm$^{-1}$ |
| aromatic | 1571 cm$^{-1}$ |
| | 1496 cm$^{-1}$ |

STAGE D: (2-benzyloxymethyl) (5-methyl) (3-phenylthio) 4-pyrone

—477 mg of the product obtained above in Stage C and—20 ml of toluene are introduced and agitated in the presence of a catalytic quantity of paratoluenesulphonic acid at a temperature of 88° C. for 6 hours.

The mixture is left to return to ambient temperature, calcium carbonate is added, followed by agitation, filtration and concentration and 350 mg of expected product is obtained in the form of an oil.

Analyses:

| IR Spectrum (CHCl$_3$) | |
|---|---|
| conjugated system | 1644 cm$^{-1}$ |
| | 1630 cm$^{-1}$ |
| aromatic | 1604 cm$^{-1}$ |
| | 1580 cm$^{-1}$–1498 cm$^{-1}$ |

STAGE E: (1-benzyl) (2-benzyloxymethyl) (5-methyl) (3-phenylthio) 4-pyridone

—310 mg of the product obtained above in Stage D
—300 mg of benzylamine and—10 ml of methanol are introduced and agitated for 48 hours at ambient temperature, the mixture is evaporated to dryness and 340 mg of expected product is obtained.

Analyses:

| IR Spectrum (CHCl$_3$) | |
|---|---|
| C=O | 1635 cm$^{-1}$ |
| C=C and | 1586 cm$^{-1}$ |
| aromatic | 1512 cm$^{-1}$ |
| | 1498 cm$^{-1}$ |

EXAMPLE 4: 2-(hydroxymethyl) 5-methyl 3-phenylthio 1-[[2'-1H-tetrazol-5-yl) (1,1'-biphenyl) 4-yl]methyl] 4-(1H) -pyridone.

STAGE A: 5-(4,-bromomethyl 1,1-biphenyl-2-yl) 1-triphenylmethyl 1H-tetrazole.

117.1 g of N-bromosuccinimide then 13.9 g of benzoyl peroxide are added to 315 g of 5-(4'-methyl 1,1-biphenyl-2-yl) 1-triphenylmethyl 1H-tetrazole described in J. Org. Chem. 991, 56, 2395 in solution in 4725 cm³ of dichlorethane, and the mixture is heated under reflux for 45 minutes. It is cooled down to 30° C., the solvent is partially distilled under reduced pressure, then 1470 cm³ of isopropyl ether is added, the solvent is again partially evaporated, agitation is maintained at 20° C. for one hour, the crystallized product is separated off, dried at 40° C. under reduced pressure for 16 hours and 316.7 g of expected product is collected.

STAGE B: 5-(4'-azidomethyl 1,1-biphenyl-2-yl) 1H-tetrazole.

11.14 g of product obtained in Stage A and 1.56 g of sodium nitride are dissolved in 200 cm³ of dimethylsulphoxide, agitation is carried out for 3 hours 30 minutes, the reaction medium is poured into ice-cooled water, extracted with ethyl acetate, the extracts are washed with salt water, dried and the solvent is evaporated under reduced pressure. 10.2 g of product is obtained, used as it is for the following stage.

STAGE C: 5-(4'-aminomethyl 1,1-biphenyl-2-yl) 1H-tetrazole.

The product obtained in Stage A is taken up in 1000 cm³ of methanol, 2 g of activated charcoal with 10% palladium is added and hydrogenation is carried out for 48 hours. The solution is filtered, rinsed with methanol and the solvent is evaporated under reduced pressure. After chromatography on silica (eluant: acetone—ethyl acetate—water.5-4-1), 3.2 g of expected product is recovered. M.p.>260° C.

STAGE D: 2-(benzyloxymethyl) 5-methyl 3-(phenylthio) 1-[[2'-(1H-tetrazol-5-yl) (1,1'-biphenyl) 4-yl]methyl] 4-(1H)-pyridinone.

1.14 g of (2-benzyloxymethyl) 5-methyl 3-phenylthio 4-pyrone described in Ann. Chem. 1985, 2261–2284 and prepared as indicated in Stage D of Example 1 and 1.14 g of the amine prepared in Stage B above are dissolved at reflux temperature in 20 cm³ of methoxy ethanol. After 24 hours under reflux, the solution is left to cool down, the solvent is evaporated, the residue is chromatographed on silica (eluant: acetone—ethyl acetate—water 5-4-1) and 0.92 g of expected product is recovered.

Analyses:

IR Spectrum (CHCl₃)
C = O 1700, approx. 1685 cm⁻¹

C = C aromatic
heteroaromatic } 1606, 1583, 1547, 1508, 1496, 1479 cm⁻¹

STAGE E: 2-(hydroxymethyl) 5-methyl 3-phenylthio 1-[[2'-(1H-tetrazol-5-yl) (1,1'-biphenyl) 4-yl] methyl] 4-(1H)-pyridone.

1.43 g of product prepared as in Stage C in 15 cm³ of acetic acid and 7.5 cm³ of concentrated hydrochloric acid are heated under reflux for 48 hours. The mixture is left to return to ambient temperature, poured into ice-cooled water, alkalized to pH=14 with concentrated soda, extraction is carried out with methylene chloride then the aqueous phase is acidified. Agitation is carried out for one hour at ambient temperature, followed by separating, washing with water, drying under reduced pressure at 50° C. and 0.5 g of expected product is collected. M.p.=160°–163° C.

Analyses:

IR Spectrum (CHCl₃)

C = O
C = C } 1632, 1603, 1581, 1539 cm⁻¹
aromatic complex absorption OH/NH region The products of Examples 2 to 90 which follow also illustrate the invention without however limiting it and correspond to formula (I) as defined above in which $R_5$ represents the —$CH_2$— radical, $R_1$, $R_2$, $R_3$ and $R_4$ have the meanings indicated in the table hereafter and Y is represented by the numbers 1, 2, 3, 4, 5, 6, 7, 8 or 9 which have the following meanings:

—the numbers 1 to 6 and 10 to 12 represent a biphenyl radical of formula:

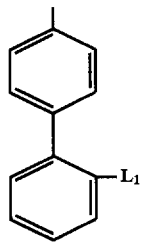

such that

—number 1 corresponds to L1 representing —CH=CH—$CO_2CH_3$

—number 2 corresponds to L1 representing —CH=CH—$CO_2H$

—number 3 corresponds to L1 representing —$CO_2CH_3$

—number 4 corresponds to L1 representing —$CO_2H$

—number 5 corresponds to L1 representing a tetrazolyl radical protected by the triphenyl methyl radical —number 6 corresponds to L1 representing a tetrazolyl radical —number 7 corresponds to L1 representing an —$SO_2$—NH—CO—NH—$CH_2$—CH=$CH_2$ radical —number 10 corresponds to L1 representing —$SO_2$—NH—CO—NH—$CH_2$—$CH_2$—$CH_3$ —number 11 corresponds to L1 representing —$SO_2$—NH—CO—$OC_2H_5$ —number 12 corresponds to L1 representing —$SO_2NH$—CO—$CH_2$—$CH_2$—$CH_3$ —numbers 8 and 9 represent a phenyl radical of formula:

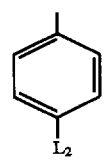

such that

—number 8 corresponds to L2 representing —$CH_2$—$CO_2CH_3$

—number 9 corresponds to L2 representing —$CH_2$—$CO_2H$

These products can be obtained according to the same processes as those indicated above.

| No Ex | R₁ | R₂ | R₃ | R₄ | Y |
|---|---|---|---|---|---|
| 1a | Me | H | SC₆H₅ | CH₂OCH₂C₆H₅ |  |
| 2 | Me | H | SC₆H₅ | CH₂OH |  |
| 3 | Me | H | SC₆H₅ | CH₂OCH₂C₆H₅ | (6) |
| 4 | Me | H | SC₆H₅ | CH₂OH | (6) |
| 5 | Me | H | SC₆H₅ | COOH | (6) |
| 6 | Me | H | SC₆H₅ | COOH | (7) |
| 7 | Me | H | SMe | CH₂OH | (6) |
| 8 | Me | H | SMe | COOH | (6) |
| 9 | Me | H | SMe | COOH | (7) |
| 10 | Bu | H | SC₆H₅ | CH₂OH | (6) |
| 11 | Bu | H | SC₆H₅ | COOH | (6) |
| 12 | Bu | H | SC₆H₅ | COOH | (7) |
| 13 | Bu | H | SMe | COOH | (6) |
| 14 | Bu | H | SMe | COOH | (7) |
| 15 | H | pyrrolidinyl | H | nBu | (3) |
| | | 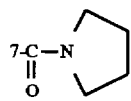 | | | |
| 16 | " | " | " | " | (4) |
| 17 | " | H | " | " | (8) |
| 18 | " | " | " | " | (9) |
| 19 | 6-CH₃ | H | " | " | (3) |
| 20 | " | " | " | " | (4) |
| 21 | H | H | " | " | (5) |
| 22 | " | " | " | " | (6) |
| 23 | | 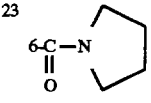 | " | " | (3) |
| 24 | " | " | " | " | (4) |
| 25 | H | 7-CO₂CH₃ | " | " | (3) |
| 26 | " | 7-CO₂H | " | " | (4) |
| 27 | 6-CH₂—S—C₆H₅ | H | " | " | (3) |
| 28 | " | " | " | " | (4) |
| 29 | H | " | " | " | (1) |
| 30 | " | " | " | " | (2) |
| 31 | " | 8-CH₃ | " | " | (3) |
| 32 | " | " | " | " | (4) |
| 33 | 6-CH₂—O—C₂H₅ | H | " | " | (3) |
| 34 | " | " | " | " | (4) |
| 35 | H | 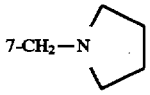 | H | nBu | (3) |
| 36 | " | " | " | " | (4) |
| 37 | H | 8-CO₂CH₃ | " | " | (5) |
| 38 | " | " | " | " | (6) |
| 39 | " | 8-CO₂H | " | " | (5) |
| 40 | " | " | " | " | (6) |
| 41 | 6-CH=CH—C₆H₅ (Z) | H | " | " | (3) |
| 42 | 6-CH=CH—C₆H₅ (Z) | " | " | " | (4) |
| 43 | H | " | " | " | (5) |
| 44 | " | " | " | " | (6) |
| 45 | 5-CH₃ | 7-CH₃ | " | " | (5) |
| 46 | " | " | " | " | (6) |
| 47 | H | 7-CO₂CH₃ | " | " | (5) |
| 48 | " | " | " | " | (6) |
| 49 | " | 7-CO₂H | " | " | (5) |

-continued

| No Ex | R₁ | R₂ | R₃ | R₄ | Y |
|---|---|---|---|---|---|
| 50 | " | " | " | " | (6) |
| 51 | " | 8-CO₂CH₃ | " | CH₃ | (5) |
| 52 | " | 8-CO₂H | " | " | (6) |
| 53 | " | 8-CO₂H | " | " | (5) |
| 54 | " | " | " | " | (6) |
| 55 | H | 7-C(=O)-O-CH₂CH₂-N(CH₃)₂ | H | nBu | (5) |
| 56 | " | " | " | " | (6) |
| 57 | 6-CH₂-S-(3-pyridyl) | H | " | " | (5) |
| 58 | " | " | " | " | (6) |
| 59 | " | 7-CH₂-C(=O)-N(pyrrolidinyl) | " | " | (3) |
| 60 | " | " | " | " | (4) |
| 61 | " | 8-CO₂CH₃ | " | C₂H₅ | (5) |
| 62 | " | " | " | " | (6) |
| 63 | " | 8-CO₂H | " | " | (5) |
| 64 | " | " | " | " | (6) |
| 65 | 6-CH=CH-C₆H₅ (E) | H | " | nBu | (3) |
| 66 | 6-CH=CH-C₆H₅ (E) | " | " | " | (4) |
| 67 | 6-CH₂-S-C₆H₅ | " | " | " | (5) |
| 68 | " | " | " | " | (6) |
| 69 | 6-CH₂-S(=O)-C₆H₅ | " | " | " | (5) |
| 70 | " | " | " | " | (6) |
| 71 | 6-CH₂-S(O)₂-C₆H₅ | " | " | " | (5) |
| 72 | " | " | " | " | (6) |
| 73 | 6-CH₂-S-CH₃ | H | H | nBu | (5) |
| 74 | " | " | " | " | (6) |
| 75 | 6-F | 7-F | 8F | " | (5) |
| 76 | " | " | " | " | (6) |
| 77 | 6-F | 7-N(pyrrolidinyl) | " | " | (5) |
| 78 | " | " | " | " | (6) |
| 79 | H | 8-CO₂CH₃ | H | H | (7) |
| 80 | " | 8-CO₂H | " | " | (7) |
| 81 | " | 8-CO₂CH₃ | " | CO₂CH₃ | (5) |
| 82 | " | 8-CO₂H | " | CO₂H | (6) |
| 83 | " | 8-CO₂CH₃ | " | nPr | (5) |
| 84 | " | 8-COOH | " | " | (6) |
| 85 | " | 8-CO₂CH₃ | " | C₂H₅ | (7) |
| 86 | " | 8-CO₂H | " | " | (7) |
| 87 | " | 8-CO₂CH₃ | " | cyclopropyle | (5) |
| 88 | " | 8-CO₂H | " | " | (6) |
| 89 | " | H | " | nPr | (5) |
| 90 | " | " | " | " | (6) |
| 91 | nPr | " | S-C₆H₅ | -CO₂-C₂H₅ | (6) |
| 92 | " | " | " | " | (7) |
| 93 | " | " | " | -CO₂H | (6) |

-continued

| No Ex | R₁ | R₂ | R₃ | R₄ | Y |
|---|---|---|---|---|---|
| 94 | " | " | " | " | (7) |
| 95 | " | " | —S—Me | " | (6) |
| 96 | " | " | " | " | (7) |
| 97 | " | " | S—C₆H₅ | " | (10) |
| 98 | " | " | " | " | (11) |
| 99 | " | " | " | " | (12) |
| 100 | " | " | —S—Me | " | (10) |
| 101 | " | " | " | " | (11) |
| 102 | " | " | " | " | (12) |

EXAMPLE 103: pharmaceutical composition

Tablets were prepared corresponding to the following formula:
Product of Example 1 . . . 10 mg
Excipient for a tablet completed at . . . 10 mg (detail of excipient: lactose, talc, starch, magnesium sterate).

We claim:

1. A compound selected from the group consisting of all possible racemic, enantiomeric and diastereoisomeric forms of a compound of the formula

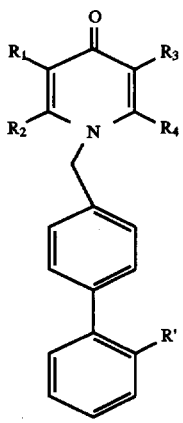

wherein one of $R_1$ and $R_3$ is hydrogen or alkyl of 1 to 6 carbon atoms and the other is selected from the group consisting of —SH, alkylthio of 1 to 6 carbon atoms and phenylthio, $R_2$ and $R_4$ are individually selected from the group consisting of hydrogen, halogen, —OH, —CN, —NO₂, sulfo, acyl and acyloxy of a carboxylic acid of up to 12 carbon atoms, alkyl, alkenyl, alkynyl and alkoxy of up to 6 carbon atoms unsubstituted or substituted by a substituent selected from the group consisting of halogen, hydroxyl, amino, mono and dialkylamino where alkyl has 1 to 4 carbon atoms, pyrrolidinyl, morpholinyl, piperidinyl, benzyl, benzyloxy and phenoxy; free, salified, amidified or esterified carboxy with an alkyl of 1 to 4 carbon atoms; pyrrolidinylcarbonyl, morpholinyl-carbonyl, carbamoyl, dialkylcarbamoyl with alkyl of up to 4 carbon atoms and piperidinyl-carbonyl; R' is selected from the group consisting of cyano, free, salified, amidified or esterified carboxy with an alkyl of up to 4 carbon atoms, tetrazolyl, isoxazolyl and —SO₂—ZC—R₁₄C where ZC is selected from the group consisting of —NH—, NH—CO—, —NHCO₂—, —NH—CO—NH— and a single bond and R₁₄C is selected from the group consisting of methyl, ethyl, propyl, vinyl, allyl, pyridyl, phenyl, benzyl, pyridylmethyl, pyridylethyl, nitropyridyl, pyrimidyl, tetrazolyl, diazolyl, piperidinyl, alkyl-piperidinyl, thiazolyl, alkylthiazolyl, tetrahydrofuranyl and methyltetrahydrofuranyl; and their addition salts with non-toxic, pharmaceutically acceptable acids or bases.

2. A compound of claim 1 wherein $R_3$ is —SH or alkylthio of 1 to 6 carbon atoms or phenylthio.

3. A compound of claim 2 wherein and $R_1$ and $R_2$ are individually selected from the group consisting of hydrogen, alkyl of up to 6 carbon atoms and free or esterified carboxy with alkyl of up to 4 carbon atoms.

4. A compound of claim 2 wherein $R_4$ is alkyl of up to 6 carbon atoms unsubstituted or substituted by a member selected from the group consisting of hydroxyl, benzyloxy and phenoxy, or is free or esterified carboxy with alkyl of up to 4 carbon atoms.

5. A compound of claim 1 wherein R' is tetrazolyl or carboxy.

6. A compound of claim 2 wherein R' is tetrazolyl or carboxy.

7. A compound of claim 1 selected from the group consisting of 2-(hydroxymethyl)-5-methyl-3-phenylthio-1-[[2'-(1H-tetrazol-5-yl)-(1,1'-biphenyl)-4-yl]-methyl]-4-(1H)-pyridone; 2-(hydroxymethyl)-5-butyl-3-phenylthio-1-[[2'-(1H-tetrazol-5-yl)-(1,1'-biphenyl)-4-yl]-methyl]-4-(1H)-pyridone; 2-(hydroxymethyl)-5-methyl-3-phenylthio-1-[[2'-(carboxyl)-(1,1,-biphenyl)-4-yl]-methyl]-4-(1H)-pyridone; and 2-(hydroxymethyl)-5-butyl-3-phenylthio-1-[[2'-(carboxyl)-(1,1,-biphenyl)-4-yl]-methyl]-4-(1H) -pyridone.

8. A composition for inhibiting angiotensin II effects comprising an amount of a compound of claim 1 for inhibiting angiotensin II effects and an inert pharmaceutical carrier.

9. A composition of for inhibiting angiotensin II effects comprising an amount of a compound of claim 4 for inhibiting angiotensin II effects and an inert pharmaceutical carrier.

10. A composition for inhibiting angiotensin II effects comprising an amount of a compound of claim 6 for inhibiting angiotensin II effects and an inert pharmaceutical carrier.

11. A composition for inhibiting angiotensin II effects comprising an amount of a compound of claim 7 for inhibiting angiotensin II effects and an inert pharmaceutical carrier.

12. A method of treating cardiovascular illnesses in warm-blooded animals comprising administering to warm-blooded animals an amount of a compound of claim 1 sufficient to treat cardiovascular illnesses.

13. A method of treating cardiovascular illnesses in warm-blooded animals comprising administering to warm-blooded animals an amount of a compound of claim 4 sufficient to treat cardiovascular illnesses.

14. A method of treating cardiovascular illnesses in warm-blooded animals comprising administering to warm-blooded animals an amount of a compound of claim 6 sufficient to treat cardiovascular illnesses.

15. A method of treating cardiovascular illnesses i warm-blooded animals comprising administering to warm-blooded animals an amount of a compound of claim 7 sufficient to treat cardiovascular illnesses.

\* \* \* \* \*